United States Patent [19]

Knifton et al.

[11] Patent Number: 4,876,397

[45] Date of Patent: Oct. 24, 1989

[54] METHOD FOR PRODUCTION OF PHENOL/ACETONE FROM CUMENE HYDROPEROXIDE

[75] Inventors: John F. Knifton; Neal J. Grice, both of Austin, Tex.

[73] Assignee: Texaco Chemical Company, White Plains, N.Y.

[21] Appl. No.: 261,819

[22] Filed: Oct. 24, 1988

[51] Int. Cl.⁴ ...................... C07C 37/08; C07C 45/53
[52] U.S. Cl. .................... 568/798; 568/485; 568/741; 568/768
[58] Field of Search ............... 568/741, 768, 798, 485

[56] References Cited

U.S. PATENT DOCUMENTS

| | | | |
|---|---|---|---|
| 2,628,984 | 2/1953 | Aller et al. | 568/798 |
| 2,715,145 | 8/1955 | Bewley et al. | 568/798 |
| 2,889,368 | 6/1959 | Hiratsuko et al. | 568/798 |
| 4,209,465 | 6/1980 | Austin et al. | 568/798 |
| 4,246,203 | 1/1981 | Wirth | 568/798 |
| 4,267,379 | 5/1981 | Austin | 568/798 |
| 4,267,380 | 5/1981 | Austin | 568/798 |

FOREIGN PATENT DOCUMENTS

| | | | |
|---|---|---|---|
| 0157531 | 12/1979 | Japan | 568/798 |
| 0992508 | 1/1983 | U.S.S.R. | 568/798 |

*Primary Examiner*—Warren B. Lone
*Attorney, Agent, or Firm*—Jack H. Park; Kenneth R. Priem; Cynthia L. Kendrick

[57] ABSTRACT

A method is disclosed for the synthesis of phenol and acetone by decomposition over a heterogeneous catalyst comprising a fluorine-containing acidic compound on an inert support. The method allows for quantitative conversions with yields of up to >99 mole %.

13 Claims, No Drawings

METHOD FOR PRODUCTION OF PHENOL/ACETONE FROM CUMENE HYDROPEROXIDE

CROSS-REFERENCE

This application is related to U.S. patent application Ser. Nos. 261,817 and 261,818.

This invention relates to a novel method for the decomposition of organic hydroperoxides, and more particularly this invention relates to a method for producing phenol and acetone by decomposition of cumene hydroperoxide over a heterogeneous catalyst. The catalyst comprises a fluorine-containing compound on a supported catalyst. The catalyst can be in the form of a fluorophosphoric acid-on-titania or hydrogen fluoride-on-titania. The invention is particularly advantageous in that there is essentially quantitative conversion of cumene hydroperoxide (>98%) under mild conditions. The catalyst is very attractive in that analysis shows essentially no by-products such as mesityl oxide or cumyl phenol which are produced in much smaller percentages than with standard acid catalysis.

BACKGROUND OF THE INVENTION

It is known to those skilled in the art that cumene can be oxidized to cumene hydroperoxide and that cumene hydroperoxide can be decomposed by various means to provide phenol and acetone.

In U.S. Pat. No. 2,889,368 to Hiratsuka there is a process discussed for the decomposition of various organic hydroperoxide substances, such as, for example, cumene hydroperoxide. The cumene hydroperoxide is decomposed in the presence of a 10 to 70% aqueous sulfuric acid solution at a temperature between about 50° and 100° C. to phenol and acetone, the yields amounting to 80–90%.

Today, the disadvantages of using soluble strong acid catalysts in this application include (a) the need for an efficient means of separating the phenol/acetone products from the acid or spent acid catalyst, (b) the need to neutralize said acids with caustic etc., (c) the disposal of salts generated as a result of said neutralization, and (d) the difficulty in obtaining >99.9% purity phenol from such a process if there is any entrainment or contamination of the crude phenol/acetone product by said acid catalyst.

U.S. Pat. No. 2,715,145 concerns a process for increasing the yield of phenol by decomposing the material contained in the peroxide acidic catalyst decomposition mixture. Again it is disclosed that the decomposition can be promoted by the addition to the residue of acids such as sulfuric acid, phosphoric acid or sulfonic acids, as well as acid washed activated earth, such as fuller's earth.

A decomposition catalyst of sulfur dioxide or sulfuric acid is also used in U.S. Pat. No. 4,016,213 to obtain phenol and acetone from cumene hydroperoxide.

In U.S. Pat. No. 4,246,203 a hydroperoxide of an aromatic compound is converted to a volatile phenol and a carbonyl compound in a cleavage decomposition reaction. Here a wide range of both solid and liquid cleavage catalysts may be used including acetic acid, sulfur dioxide, sulfur, formic acid, phosphoric acid and flouroboric acid, although sulfuric acid is preferred. Silica/alumina gave rather poor yields of phenol and acetone under these conditions.

Lewis acid catalysts were employed in the invention of U.S. Pat. No. 4,267,380, to Austin et al, to decompose cumene hydroperoxide to phenol and acetone. Some Lewis acids were unsatisfactory or, in some cases, found to be catalytically inert. Preferred Lewis acids were tungsten hexafluoride, silicon tetrafluoride, stannous chloride, stannic fluoride, antimony pentachloride, sulfur monochloride and sulfur tetrafluoride.

In U.S. Pat. No. 4,209,465, also to Austin et al, it was found that cumene hydroperoxide could be decomposed to phenol and acetone using an isolable carbonium, tropylium or oxonium salt, such as triphenylcarbonium tetrafluoroborate, as the catalyst.

In another patent to Austin et al, U.S. Pat. No. 4,267,379, cumene hydroperoxide is decomposed to phenol and acetone using boron trifluoride or boron trifluoride complexed with an oxygen-containing polar compound.

In U.S. Pat. No. 4,358,618 there is described a process for decomposing a cumene oxidation product mixture by mixing the product with an acid that lowers the cumene hydroperoxide concentration and converts most of the dimethylphenol carbinol to dicumyl peroxide.

In an article by Augustin et al, in *Stud. Univ. Babes–Bolyai, Chem.* 1986, 31, 19–23 (see Chem. Abstracts 107:236170j, 1987), "The Life Of Synthetic Aluminosilicate Catalysts In The Decomposition Of Cumene Hydroperoxide" was studied.

In U.S. Pat. No. 4,743,573 to Romano there are described catalysts for the selective decomposition of cumene hydroperoxide into phenol and acetone which comprise oxide forms of silicon, aluminum and boron in the form of crystals having a structure of zeolite wherein aluminum and boron replace silicon in the crystalline structure of silica and wherein the crystals are interconnected by oligomeric silica. The phenol selectivity is typically 80.5 to 96% with these catalysts in batch studies, and higher than 98% in continuous synthesis at cumene hydroperoxide conversion levels of 90%.

European patent application No. 203-632-A describes a catalyst for decomposition of cumene hydroperoxide to produce phenol and acetone comprising zeolite crystals containing boron and aluminum bonded with silica. A portion of the silicon atoms in the crystal lattice of silica are replaced by Al and B and the zeolite crystals are bonded to each other by a siliceous bonding agent which allows the catalyst to assume the shape of mechanically stable microspheres.

Carboxylic acid derivatives have also been used to catalyze cumene hydroperoxide decomposition. See *Izv. Akad. Nauk Turkm.* 5512, Ser. Fiz.—Tekh, Khim, Geol. Nauk 1987, (2), 108–10 (Russ) and Chem. Abstracts 108:55583w (1988).

Molybdenum, vandium and titanium catalysts have also been used for the catalytic decomposition of cumyl hydroperoxide to yield mainly phenol and acetone. See Stozhkova, G. A., et al. (Yarosl. Politekh. Inst., Yaroslavl, USSR) *Neftekhimiya* 1987, 27(1), 137–41 (Russ) and Chem. Abstracts 107:197676g (1987).

In the cases where acidic substances are utilized as the catalysts the yields are satisfactory, however many of these acid catalysts require substantial expenditure for production of phenol and acetone, there are disposal problems with spent acids or their salts, and there are difficulties in achieving >99.9% purity phenol required by today's market place due to entrainment or breakthrough of said acids. In addition, by-products such as mesityl oxide, α-methylstyrene, acetophenone and 2-phenyl-2-propanol and produced along with the product and must somehow be removed and processed.

It would be a substantial advance in the art if phenol and acetone could be produced in yields approaching 100% by decomposition over a heterogeneous catalyst using mild conditions. A catalyst which worked at high space velocities using mild conditions and yet afforded high selectivities and yields with a smaller percentage of by-products would be particularly advantageous. Furthermore a very active, long life heterogeneous catalyst would also solve the catalyst disposal and acid entrainment problems cited above.

SUMMARY OF THE INVENTION

In accordance with certain of its aspects, the novel method of this invention for continuous cogeneration of phenol and acetone comprises reacting cumene hydroperoxide in the presence of a fluorine-containing heterogeneous catalyst. Particularly effective are fluorophosphoric acids and hydrogen fluoride, preferably on an inert, high surface area support, such as titania, using mild conditions. Examples demonstrate the superior performance of fluorophosphoric acids-on-titania versus non-fluoride, phosphoric acids-on-titania.

A particular advantage of the instant invention over the prior art is that it has been discovered in the instant invention that fluorine-containing heterogeneous catalysts have properties which allow for distinct improvements over the use of $H_2SO_4$ and $SO_2$. The method of the invention gives essentially quantitative conversion of cumene hydroperoxide under mild conditions with phenol and acetone as the major product fractions. Essentially no mesityl oxide or cumyl phenol by-products are observed in certain continuous runs.

DESCRIPTION OF THE INVENTION

Preparation of the product of this invention may be carried out typically by reacting cumene hydroperoxide in the presence of a heterogeneous catalyst comprising a fluorine-containing compound on an inert support. The decomposition is carried out continuously and the catalyst preferably comprises a fluorine-containing compound on an inert, high surface area support.

The reaction can be represented by the following:

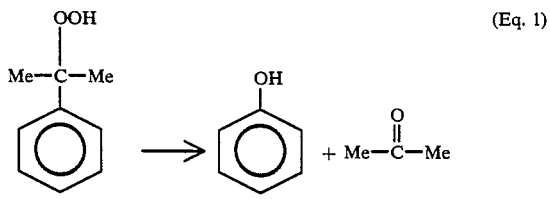

(Eq. 1)

The catalysts used to effect this reaction are preferably fluorine-containing compounds on titania. The catalysts are effective in the form of powders, granules or extrudates.

The fluorine impregnated on the catalyst in the instant invention can be present as a hydrogen fluoride group or fluorophosphoric acid group which is chemically bound to the titania support. In the latter case, the exact nature of the bonding is not fully understood, but is believed to include, for the fluorophosphoric acids-on-titania catalysts, the following:

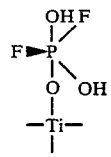

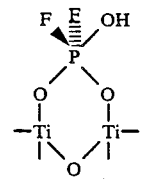

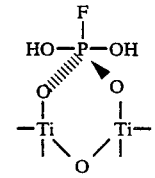

Said fluorine may be introduced onto the inert support as a fluorine-containing acid compound. The same fluorine may, for example, be introduced as a substituted phosphoric acid, such as a fluorophosphoric acid, including fluorophosphoric acid, $FPO_3H_2$ and difluorophosphoric acid $F_2PO_2H$. Also effective are acids such as hydrogen fluoride and aqueous hydrofluoric acid.

The support should preferably comprise an inert compound. Compounds which may be employed are those containing elements of Group III and IV of the Periodic Table. Suitable compounds include the oxides of aluminum, silicon, titanium and zirconium or combinations thereof, e.g. alumina, silica (silicon dioxide), titania (titanium dioxide) and zirconia, as well as combinations thereof. Also suitable are carbon, ion-exchange resins and carbon-containing supports. Good results were observed using $TiO_2$ as the support.

The inert support may be in the form of powders, pellets, spheres, shapes and extrudates. As will be demonstrated by the examples, the supports are preferably of high purity and high surface area. It has been found in the process of this invention that greater conversion of cumene hydroperoxide is achieved where the surface area of the support is generally $> 10$ m$^2$/g.

The reaction may be carried out in either a stirred slurry reactor or in a fixed bed continuous flow reactor. The catalyst concentration should be sufficient to provide the desired catalytic effect.

The weight percent of fluorine of Group III/Group IV support should be such that the concentration of the fluorine-containing compound in the formulated catalyst is in the range of 0.1 wt% to 20 wt%, although concentrations outside this range may also be employed. Where the fluorine is, for example, difluorophosphoric acid, supported on titania, a suitable quantity of fluorine is 0.1-10 wt%.

Cumene hydroperoxide decomposition may be conducted batchwise, in a continuous slurry bed reactor, or in a fixed-bed, continuous flow, reactor. For practical reasons a fixed bed process is preferred. In all cases the catalyst concentration should be sufficient to provide the desired catalytic effect.

Cogeneration of phenol and acetone can generally be conducted at temperatures from 20° to 150° C.; the preferred range is 40° to 120° C. The operating pressure may be from zero to 1000 psig, or higher. The preferred pressure range is 100 to 400 psig. Because of the highly exothermic nature (52 kal/mole) of the cumene hydroperoxide decomposition (Eq. 1), temperature control is particularly important, especially in a fixed catalyst process.

Typically, phenol is generated continuously in up to ca. 60 wt% concentration in the crude product liquid effluent, and likewise, acetone may be generated in 40 wt% concentrations. The cumene hydroperoxide should preferably be as pure as possible, but a 60–80% purity is certainly acceptable. Typical impurities in such an "80%" cumene hydroperoxide feed are cumene, 2-phenyl-2-propanol and acetophenone. Said cumene hydroperoxide is generally diluted with inert solvent, or product, prior to being fed to the decomposer. Typical diluents include acetone, or a mix of acetone, cumene and/or phenol.

Generally cumene hydroperoxide conversions are quantitative in continuous unit operations. Phenol yields, based on hydroperoxide charged, are >99 mole%. Likewise, acetone yields are also 99 mole% or better.

These yields are achieved at total liquid hourly space velocities (LHSV) of one to 10 under mild conditions. Continuous generation of phenol/acetone in a plug flow reactor at LHSV's of 1–4 have been demonstrated, for example, with fluorophosphoric acid-on-titania.

Here LHSV is defined as follows:

$$LHSV = \frac{\text{Weight Of Total Liquid Feed Run Through The Reactor Per Hour}}{\text{Volume of Catalyst In Reactor}}$$

Conversion of cumene hydroperoxide (wt%) is estimated in the following examples using the equation:

$$\frac{[\text{Wt \% Conc. of } (C_6H_5C(CH_3)_2OOH \text{ in Feed} - \text{Wt \% Conc. of Cumene Hydroperoxide in product}]}{\text{Wt \% Conc. of Cumene Hydroperoxide in Feed}} \times 100$$

The data of Example 1 illustrates the quantitative conversion of cumene hydroperoxide to phenol/acetone catalyzed by difluorophosphoric acid-on-titania. The reaction is conducted under mild conditions. Minor by-products include α-methyl styrene. During the run 2-phenyl-2-propanol is also apparently consumed.

Table I illustrates:

(a) The good performance of other fluorine-on-titania catalysts, e.g. $FPO_3H_2/TiO_2$ and $HF/TiO_2$ (Ex. 2 and 3).

(b) The superior performance of fluorophosphoric acid-on-titania versus non-fluoride, phosphoric acid-on-titania (cf. Ex. 1, 2 and 3 vs. 4).

Table II illustrates the continuous generation of phenol/acetone using the fluorophosphoric acid-on-titania catalyst and a cumene hydroperoxide feed diluted with acetone. Cumyl hydroperoxide conversion is >75% throughout this run. It is considered significant that very little (> or =0.1%) mesityl oxide is found in these products, while α-methyl styrene production is only modest, and the concentration of 2-phenyl-2-propanol is lower than in the feedstock.

Table III illustrates the continuous generation of phenol/acetone using the same fluorophosphoric acid-on-titania catalyst and a cumene hydroperoxide feed diluted with phenol/cumene/acetone mix. Here cumyl hydroperoxide conversion is essentially quantitative, there is no mesityl oxide formation and only trace quantities of cumyl phenol. 2-phenyl-2-propanol in the feed is also almost completely consumed.

Table IV shows a very similar experiment with the same feedstock, but employing the hydrogen fluoride-on-titania catalyst.

Attached also are descriptions of the preparation of the difluorophosphoric acid-on-titania, fluorophosphoric acid-on-titania and hydrogen fluoride on-titania catalysts employed in this work (Examples 1–7).

EXAMPLE 1

To a 250-ml round bottom flask fitted with a condenser, heater, stirrer and feed control, is charged a mixture of 60.0 g of acetone and 5.0 g of difluorophosphoric acid-on-titania (Example 9, 0.5% F, 0.6% P). The mixture is heated to reflux (57° C.) with stirring and 40.0 g of "80%" cumene hydroperoxide solution[a] added dropwise at a rate such that the pot temperature does not exceed 80° C. After the peroxide addition is complete, the mixture is heated to reflux for 2 hours further.

Upon cooling, the product mix is weighed (103.3 g) and the product liquid volume (114 ml) neutralized with sodium bicarbonate and analyzed by glc.

Analysis shows the product to have the following composition (wt%):

| | |
|---|---|
| Acetone | 71.4 |
| Phenol | 19.1 |
| Cumene | 6.9 |
| α-methyl styrene | 0.7 |
| Acetophenone | 0.3 |
| 2-phenol-2-propanol | 1.2 |
| Cumene hydroperoxide | 0.4 |
| [a]Feed Composition (wt %): | |
| Cumene hydroperoxide | 78.5 |
| Cumene | 16.5 |
| 2-phenyl-2-propanol | 4.7 |
| Acetophenone | 0.4 |
| Estimated cumene hydroperoxide conversion: >98% | |
| Estimated yield of phenol (basis hydroperoxide charged) is: 97 mole %. | |

EXAMPLES 2–4

Following the procedures of Example 1, three other heterogeneous catalysts were evaluated for phenol, acetone production from cumyl hydroperoxide. Results are summarized in Table I.

EXAMPLE 5

To a 200 ml capacity continuous plug-flow reactor, fitted with heating, cooling and feed control, is charged a fluorophosphoric acid-on-titania catalyst (Example 8, 1.8% P, 0.5% F, 150 ml). The catalyst is pretreated with acetone at 60° C., and then fed a mixture of acetone (2100 g) and 80% cumene hydroperoxide (900 g) at 150 g/hr, 60° C. and 300 psi pressure. The run is continued for 5 days with little apparent loss in catalyst activity.

The results from glc analysis of samples taken periodically over that 5 day period are summarized in Table II.

EXAMPLE 6

To the same 200 ml capacity reactor of Example 5 is charged another sample of fluorophosphoric acid-on-titania catalyst, Example 8 (150 ml). Again the catalyst is pretreated with acetone at 60° C. for about 2 hours, but this time it is followed by a feed mixture of "80%" cumene hydroperoxide (90 g) in acetone/cumene/phenol (64:24:92, 2100 g). Operating conditions are 60° C., 300 psi, 150 g/hr liquid feed rate. The run is continued for 6 days with one shut down. There is no apparent loss in catalyst activity basis the phenol and acetone estimated to be produced.

The results from GLC analysis of samples taken during this 6 day period are summarized in Table III.

For a typical product sample (#4):
Estimated yield of phenol (basis cumene hydroperoxide charged) = >99 mole%
Estimated yield of acetone (basis cumene hydroperoxide charged) = 95 mole%.

For Produce Sample #22:
Estimated Yield of Phenol = >99 mole%
Estimated Yield of Acetone = >99 mole%

EXAMPLE 7

To the same 200 ml capacity reactor of Example 5 is charged a sample of hydrogen fluorine-on-titania catalyst (Example 10, 150 ml). Again the catalyst is pretreated with acetone at 60° C. for about 2 hours, followed by a feed mixture of 80% cumene hydroperoxide (900 g) in acetone/cumene/phenol (64:24:92, 2100 g). Operating conditions are 60° C., 300 psi, 150 g/hr liquid feed rate. The run is continued for 3 days. Results from glc analysis of samples taken during this period are summarized in Table IV.

For a typical product sample (#8):
Estimated yield of phenol (basis cumene hydroperoxide charged) = 97 mole%.
Estimated yield of acetone (basis cumene hydroperoxide charged) = 93 mole%.

EXAMPLE 8

Catalyst preparation

Fluorophosphoric Acid-On-Titania

A preformed titanium dioxide catalyst support, Norton 64701, having a surface area of ca. 60 $m^2/g$ (178 g, 200 cc) was placed in 1 liter roundbottom flask. A solution of fluorophosphoric acid (11.5 g) in 80 cc of reagent acetone (62 g) was added. The flask was placed on a rotary evaporator and evacuated to aspirator vacuum then heated to 55° C. for 1 hour with periodic stirring. The resultant mixture was placed in a glass tube 1"×2" and heated to 150° C. for 30 min. Thereafter, it was heated at 350° C. under nitrogen flow for 2 hours. Both the calcined and uncalcined catalyst contained 2% P by AA.

EXAMPLE 9

II. Catalyst preparation

Difluorophosphoric Acid-On-Titania

A nearly identical support, Norton 64775 having a surface area of 51 $m^2/g$ (240 g, 220 cc) was dehydrated by heating at 0.1 mm pressure at 80° C. for 45 min. The support was placed in a polypropylene bowl and a solution of difluorophosphoric acid (17 g) in 125 cc of reagent acetone (96 g) was poured over it. The mixture was stirred for 15 minutes with a polypropylene rod, then transferred to a polypropylene beaker and placed in a desiccator where excess solvent was removed under vacuum with periodic removal from the desiccator for stirring. The mixture was then placed in a 1 liter round-bottom flask and heated under vacuum at 80° C. on a rotary evaporator for 1 hour. It was then calcined as above, at 150° C. for 1 hour and under nitrogen flow at 350° C. for 3 hours. The calcined catalyst contained 0.6% phosphorus by AA and 0.5% F by ion chromatography following oxygen combustion.

EXAMPLE 10

Catalyst preparation

Hydrofluoric Acid-On-Titania

The same support as in the previous preparation, Norton 64775 (200 g) was similarly dried at 110° C. for 1 hour then treated in the same way as in Example 9 with a solution of 48% hydrofluoric acid (9 g) in 85 cc of acetone (66 g). The recovered solids were then calcined at 150° and 350° C. under a flow of nitrogen. Fluorine content is about 1%.

TABLE I

| | | PHENOL/ACETONE GENERATION - BATCH STUDIES | | | | | | | |
|---|---|---|---|---|---|---|---|---|---|
| | | ←Product Composition (Wt %)→ | | | | | | | |
| Ex. | Catalyst | Acetone | Mesityl Oxide | Cumene | α-Methyl Styrene | Phenol | 2-Phenyl-2-Propanol | Aceto-phenone | Cumene Hydro-peroxide |
| 2 | FPO$_3$H$_2$/TiO$_2$a | 71.7 | — | 6.8 | 6.8 | 18.7 | 1.1 | 0.3 | 0.5 |
| 3 | HF/TiO$_2$b | 72.0 | — | 6.2 | 0.6 | 20.3 | 0.6 | 0.2 | <0.1 |
| 4 | H$_3$PO$_4$/TiO$_2$c | 63.8 | — | 7.0 | | 3.6 | 2.2 | 0.2 | 23.2 | a Fluorophosphoric acid-on-titania, prepared by the method of Example 8.
b Hydrogen fluoride-on-titania, prepared by the method of Example 10.
c Phosphoric acid-on-titania.

TABLE II
PHENOL/ACETONE GENERATION - CONTINUOUS STUDIES

| Ex. | Catalyst | Temp. (°C.) Dow Therm | Bed | Feed Rate (g/hr) | Pres. (psi) | Sample | Acetone | Mesityl Oxide | Cumene | Phenol | α-methyl Styrene | Aceto-Phenone | 2-Phenyl 2-Propanol | Cumene Hydro-peroxide | Day |
|---|---|---|---|---|---|---|---|---|---|---|---|---|---|---|---|
| 5 | FPO$_3$H$_2$TiO$_2$[a] | 60 | 60-74 | 150 | 300 | 2 | 80.6 | — | 3.6 | 13.5 | 1.3 | 0.2 | 0.4 | 0.1 | 1 |
| | | | 60-74 | | | 4 | 80.6 | — | 3.6 | 13.3 | 1.5 | 0.3 | 0.4 | 0.1 | |
| | | | 60-73 | | | 7 | 80.2 | — | 3.7 | 13.5 | 1.4 | 0.3 | 0.5 | 0.2 | 2 |
| | | | 60-73 | | | 11 | 79.4 | 0.1 | 3.8 | 14.0 | 1.4 | 0.3 | 0.6 | 0.2 | |
| | | | 60-72 | | | 15 | 80.4 | — | 3.6 | 13.2 | 1.3 | 0.3 | 0.7 | 0.3 | 3 |
| | | | 60-72 | | | 18 | 80.4 | — | 3.6 | 13.1 | 1.3 | 0.7 | 0.1 | 0.3 | |
| | | 60 | 59-74 | 600 | 300 | 1 | 75.1 | 0.1 | 4.2 | 12.9 | 0.5 | 0.3 | 1.3 | 5.4 | 4 |
| | | | 60-75 | | | 4 | 79.0 | 0.1 | 3.6 | 10.6 | 0.5 | 0.2 | 1.1 | 4.7 | |
| | | | 60-74 | | | 5 | 79.0 | 0.1 | 3.6 | 10.2 | 0.4 | 0.2 | 1.1 | 5.1 | 5 |
| | | | 60-73 | | | 8 | 79.3 | | 3.5 | 10.1 | 0.4 | 0.2 | 1.2 | 5.0 | |
| | | | | | | | 72.4 | | 3.5 | | | 0.1 | 1.4 | 22.5 | |

Feed Composition:

[a]Fluorophosphoric acid-on-titania catalyst, prepared by the method of Example 8.

TABLE III

PHENOL/ACETONE GENERATION - CONTINUOUS

| Ex. | Catalyst | Temp. (°C.) Dow Therm | Bed | Feed Rate (g/hr) | Sample | Acetone | Mesityl Oxide | Cumene | Phenol | α-methyl Styrene | Aceto-Phenone | 2-Phenyl 2-Pro-panol | Cumene Hydro-peroxide | 4-Cumyl Phenol | Day |
|---|---|---|---|---|---|---|---|---|---|---|---|---|---|---|---|
| 6 | FPO$_3$H$_2$TiO$_2$[a] | 60 | 60-75 | 150 | 2 | 23.6 | — | 15.3 | 60.6 | — | 0.2 | — | — | 0.1 | 1 |
|   |   |   | 60-75 |   | 3 | 32.8 | — | 14.3 | 50.9 | 1.4 | 0.2 | 0.1 | — | 0.1 | 2 |
|   |   |   | 60-75 |   | 4 | 32.7 | — | 14.2 | 52.6 | — | 0.2 | 0.1 | — | — | 3 |
|   |   |   | 60-75 |   | 6 | 32.6 | — | 14.2 | 52.7 | — | 0.2 | 0.1 | — | —[b] |   |
|   |   |   | 60-74 |   | 8 | 32.9 | — | 14.1 | 51.0 | 1.5 | 0.2 | 0.1 | — | — |   |
|   |   |   | 60-74 |   | 10 | 33.1 | — | 14.1 | 50.9 | 1.5 | 0.2 | 0.1 | — | — | 4 |
|   |   |   | 60-73 |   | 11 | 32.9 | — | 14.1 | 51.0 | 1.4 | 0.2 | 0.1 | — | — |   |
|   |   |   | 60-73 |   | 14 | 33.2 | — | 14.1 | 50.8 | 1.5 | 0.2 | 0.1 | 0.1 | — | 5 |
|   |   |   | 60-72 |   | 15 | 33.3 | — | 14.0 | 50.9 | 1.4 | 0.2 | 0.1 | 0.1 | — |   |
|   |   |   | 60-71 |   | 18 | 32.7 | — | 14.1 | 51.1 | 1.5 | 0.2 | 0.1 | 0.1 | — |   |
|   |   |   | 60-70 |   | 22 | 33.0 | — | 14.2 | 50.8 | 1.4 | 0.2 | 0.2 | 0.1 | — | 6 |
| Feed Composition: |   |   |   |   |   | 23.9 |   | 14.0 | 36.9 |   | 0.1 | 1.5 | 23.5 | — |   |

[a] Fluorophosphoric acid-on-titania, prepared by the method of Example 8.
[b] Shut down for weekend.

TABLE IV

PHENOL/ACETONE GENERATION - CONTINUOUS

| Ex. | Catalyst | Temp. (°C) Dow Therm | Bed | Feed Rate (g/hr) | Sample | Acetone | Mesityl Oxide | Cumene | Phenol | α-methyl Styrene | Aceto-Phenone | 2-Phenyl 2-Propanol | Cumene Hydro-peroxide | 4-Cumyl Phenol | Day |
|---|---|---|---|---|---|---|---|---|---|---|---|---|---|---|---|
| 7 | HF/TiO$_2$$^a$ | 60 | 60-73 | 150 | 1 | 32.9 | — | 14.3 | 51.0 | 1.2 | 0.2 | 0.1 | — | — | 1 |
|   |   |   | 60-72 | 2 |   | 31.7 | 14.2 | 52.2 | 1.4 | 0.2 | 0.1 | — | — | 0.2 |   |
|   |   |   | 60-67 |   | 4 | 33.1 | — | 14.0 | 51.0 | 1.4 | 0.2 | 0.1 | — | — | 2 |
|   |   |   | 61-68 |   | 7 | 33.2 | — | 14.0 | 51.0 | 1.3 | 0.2 | 0.2 | — | — |   |
|   |   |   | 58-63 |   | 8 | 32.5 | — | 14.5 | 51.1 | 1.1 | 0.2 | 0.4 | 0.1 | — | 3 |
|   |   |   | 61-66 |   | 11 | 32.6 | — | 14.2 | 50.1 | 1.2 | 0.2 | 0.5 | 1.0 | — |   |
| Feed Composition: |   |   |   |   |   | 24.3 |   | 13.9 | 37.2 |   | 0.1 | 1.4 | 23.0 |   |   |

$^a$Hydrogen fluoride-on-titania, prepared by the method of Exmaple 10.

What is claimed is:

1. In a method for cosynthesis of phenol and acetone by acid-catalyzed decomposition over a catalyst, the improvement comprising reacting cumene hydroperoxide over a heterogeneous catalyst consisting of a compound from the group consisting of fluorophophoric acids and hydrogen fluorides on an inert support at a temperature of about 20° C. to 150° C. and a pressure of from zero to 1000 psig.

2. The method of claim 1 wherein the fluorophosphoric acid is selected from the group consisting of difluorophosphoric acid and fluorophosphoric acid.

3. The method of claim 1 wherein the fluorine-containing acid compound is difluorophosphoric acid.

4. The method of claim 1 wherein the inert support is an oxide selected from the group consisting of titanium dioxide, alumina and silica.

5. The method of claim 1 wherein the wt% concentration of fluorine-containing compound in the formulated catalyst is in the range of 0.1 to 20 wt%.

6. The method of claim 6 wherein said titanium dioxide support has a surface area of $>10$ m$^2$/g.

7. The method of claim 1 wherein the fluorine-containing compound is fluorophosphoric acid, the support is titanium dioxide and the fluorine content in the heterogeneous catalyst is 0.1 to 10 wt%.

8. The method of claim 1 wherein the fluorine-containing compound is hydrogen fluoride, the support is titanium dioxide and the fluorine content in the formulated catalyst is in the range of 0.1 to 10 wt%.

9. The method of claim 1 wherein phenol/acetone are produced continuously and the feed liquid hourly space velocity (LHSV) is between 1 and 10.

10. The method of claim 1 wherein the temperature is between 40° and 120° C.

11. The method of claim 1 wherein the operating pressure is from 100 psig and 400 psig.

12. The method of claim 1 wherein the cumene hydroperoxide feed has a purity of at least 60%.

13. The method of claim 1 wherein the cumene hydroperoxide feed is diluted with a solvent from the group consisting of acetone or a mix of acetone, cumene and/or phenol.

* * * * *

UNITED STATES PATENT AND TRADEMARK OFFICE
CERTIFICATE OF CORRECTION

PATENT NO. : 4,876,397
DATED : October 24, 1989
INVENTOR(S) : John Frederick Knifton and Neal John Grice It is certified that error appears in the above-identified patent and that said Letters Patent is hereby corrected as shown below:

Claim 1, Col. 15, Line 6 delete the word "fluorophophoric" and substitute therefor --fluorophosphoric--.

Signed and Sealed this

Twenty-first Day of August, 1990

Attest:

HARRY F. MANBECK, JR.

*Attesting Officer*      *Commissioner of Patents and Trademarks*